US00PP34769P2

(12) United States Plant Patent
NeSmith

(10) Patent No.: US PP34,769 P2
(45) Date of Patent: Nov. 29, 2022

(54) SOUTHERN HIGHBUSH BLUEBERRY PLANT NAMED 'TH-1241'

(50) Latin Name: *Vaccinium corymbosum*
Varietal Denomination: 'TH-1241'

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/575,385

(22) Filed: Jan. 13, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ... A01H 5/08; A01H 5/02; A01H 5/00; A01H 6/36; A01H 6/368
See application file for complete search history.

*Primary Examiner* — June Hwu
(74) *Attorney, Agent, or Firm* — Thomas Horstemeyer, LLP

(57) ABSTRACT

A new and distinct cultivar of *Vaccinium* plant named 'TH-1241', characterized by a combination of early season ripening and short fruit development period; large berries with good color and flavor; highly vigorous growth; and a medium chilling requirement of about 350-450 hours, or more, below about 45° F.

6 Drawing Sheets

Botanical designation: *Vaccinium corymbosum.*
Cultivar denomination: 'TH-1241'.

BACKGROUND OF THE INVENTION

The present invention relates to a new and distinct cultivar of southern highbush blueberry plant, botanically know as *Vaccinium corymbosum*, and hereinafter referred to by the cultivar name 'TH-1241'.

The new *Vaccinium corymbosum* 'TH-1241' was first identified in 2010 in Griffin, Ga. The new variety 'TH-1241' is early season and has a short fruit development period (54 days) as compared to other early season cultivars. 'TH-1241' has large berries with very good flavor. It is estimated to have a chilling requirement of 350 to 450 hours, or more, below 45° F. when produced under typical low to mid chill production areas in temperate regions. 'TH-1241' is able to produce high-quality fruit when grown in conventional production areas.

'TH-1241' is a product of a cross of 'Star' X 'Bladen' (non-patented cultivar) made in 2007 by D. Scott NeSmith. The new blueberry plant variety 'TH-1241' has been tested in asexually propagated (by softwood vegetative cuttings from current year's growth) plantings in Alapaha, Ga. since 2011 where it was established for testing and comparing to industry standards. Observations of the resulting 'TH-1241' progeny have shown that the unique features of this new *Vaccinium corymbosum* 'TH-1241' are stable and reproduced true to type in successive generations.

SUMMARY OF THE INVENTION

The new *Vaccinium* cultivar 'TH-1241' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium corymbosum* cultivar named 'TH-1241'. In combination, these traits set 'TH-1241' apart from all other existing varieties of southern highbush blueberry known to the inventor:

1. early season in South Georgia, ripening before 'Bladen' (non-patented cultivar), flowering at the time of early variety 'Star' (U.S. Plant Pat. No. 10,675) but ripening more than a week earlier and ripening near the time of another early variety 'Rebel' (U.S. Plant Pat. No. 18,138) but flowering later as a result of a short fruit development period (about 54 days) compared to 'Star' (about 63 days) and 'Rebel' (about 62 days);
2. produces berries that are larger, more vibrant in color, with flavor having more balanced acidity to sweetness, and a shorter fruit development period than 'Star' and 'Rebel' (U.S. Plant Pat. No. 18,138);
3. highly vigorous growth that is more vigorous than 'Star' and 'Bladen'; and
4. low chilling requirement of about 350-450 hours, or more, below about 45° F. (based on comparison of flowering dates with those of known standard cultivars) when produced under typical low to mid chill production areas in temperate regions;

Comparison: As compared to the female parent 'Star', plants of *Vaccinium* 'TH-1241' have larger berry size, a drier picking scar, lighter blue color, and flavor with more balanced acidity to sweetness, are more vigorous and ripen earlier.

As compared to the male parent 'Bladen', plants of *Vaccinium* 'TH-1241' have larger berry size, similar color and flavor, and earlier flowering and ripening times.

Plants of the new *Vaccinium* can also be compared to the commercial early season southern highbush blueberry cultivar 'Rebel'. The new variety is early season and begins ripening near the time of 'Rebel', but flowers more than a week later. 'TH-1241' has berries that are larger and have lighter blue color than 'Rebel' at Alapaha, Ga. (Table 1). When compared to 'Rebel', fruit of 'TH-1241' has flavor with more balanced acidity to sweetness, and the plant is more vigorous (Table 1). No notable diseases or other pest problems have been observed for the new variety that are not also common for other varieties. The new variety is estimated to have a chilling requirement of about 350-450 hours, or more, below about 45° F. (based on comparison of flowering dates with those of known standard cultivars) when produced under typical low to mid chill production regions. Additional comparison data of 'TH-1241' with 'Rebel' are presented in the tables below.

TABLE 1

Plant and fruit ratings for 'TH-1241' and standards grown in Alapaha, GA. Data represents a 3 Year average (2014, 2015, and 2016). Rating scales are based on a 1 to 10 score, with 1 being the least desirable and 10 being the most desirable. Plants were established in 2011.

| | 'Star' | 'Rebel' | 'TH-1241' |
|---|---|---|---|
| Berry size | 7.3 | 7.8 | 8.2 |
| Berry scar | 7.0 | 7.5 | 7.3 |
| Berry color | 7.2 | 7.2 | 7.8 |
| Berry firmness | 7.5 | 7.5 | 7.5 |
| Berry flavor | 7.0 | 6.3 | 8.0 |
| Cropping | 5.0 | 5.5 | 5.0 |
| Plant vigor | 7.0 | 7.5 | 8.0 |
| Date of 50% flowering | March 6 | February 27 | March 7 |
| Date of 50% ripening | May 7 | April 30 | April 30 |
| Fruit development period (days) | 63 | 62 | 54 |

BRIEF DESCRIPTION OF THE DRAWINGS

The accompanying colored photographic illustrations show the overall appearance and distinct characteristics of the new cultivar of *Vaccinium corymbosum* 'TH-1241' showing the colors as true as possible. Colors in the photographs may differ slightly from the color values cited in the detailed botanical description, which accurately describes the colors of the new *Vaccinium corymbosum* 'TH-1241'. Photographs were taken of plants grown outdoors in Alapaha, Ga. during different years.

The photograph labeled

Figure 1:
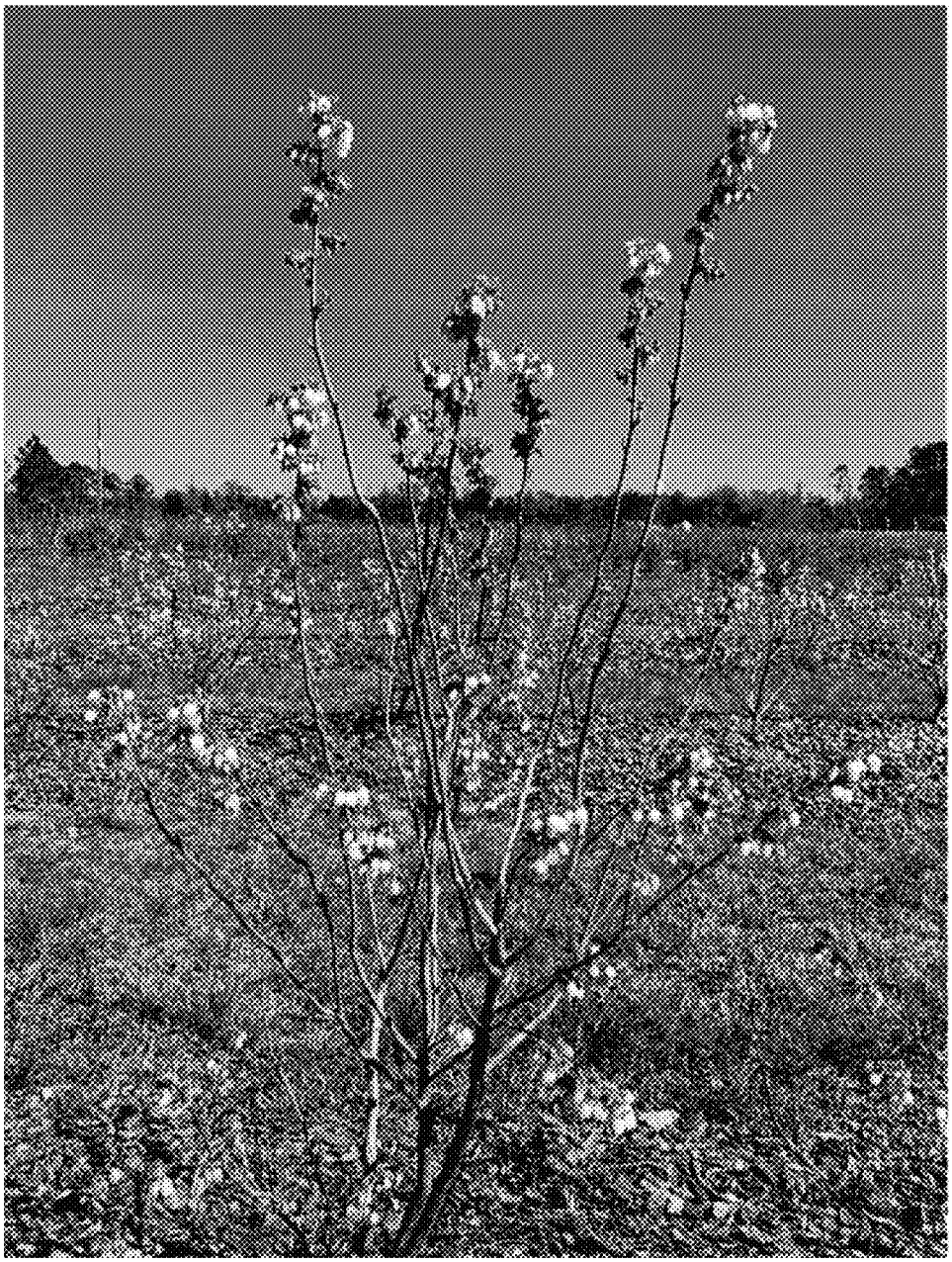
FIG. 1 depicts 3-year old plants of 'TH-1241' during flowering. Photographs were taken in March 2021.
Figure 2:
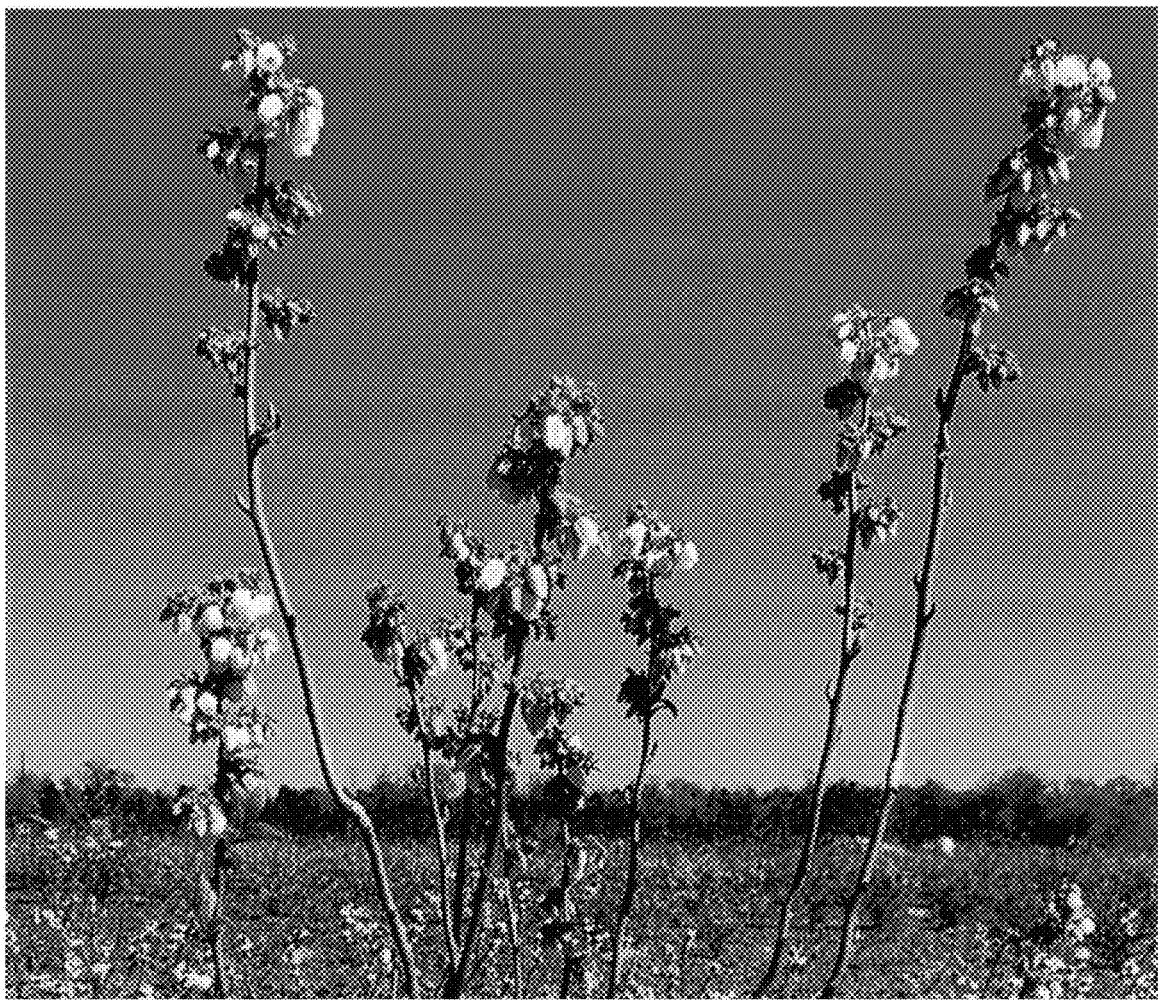

The photograph labeled FIG. 2 was taken in March 2021 and shows a close-up of flowering branches of 'TH-1241'.

Figure 3:
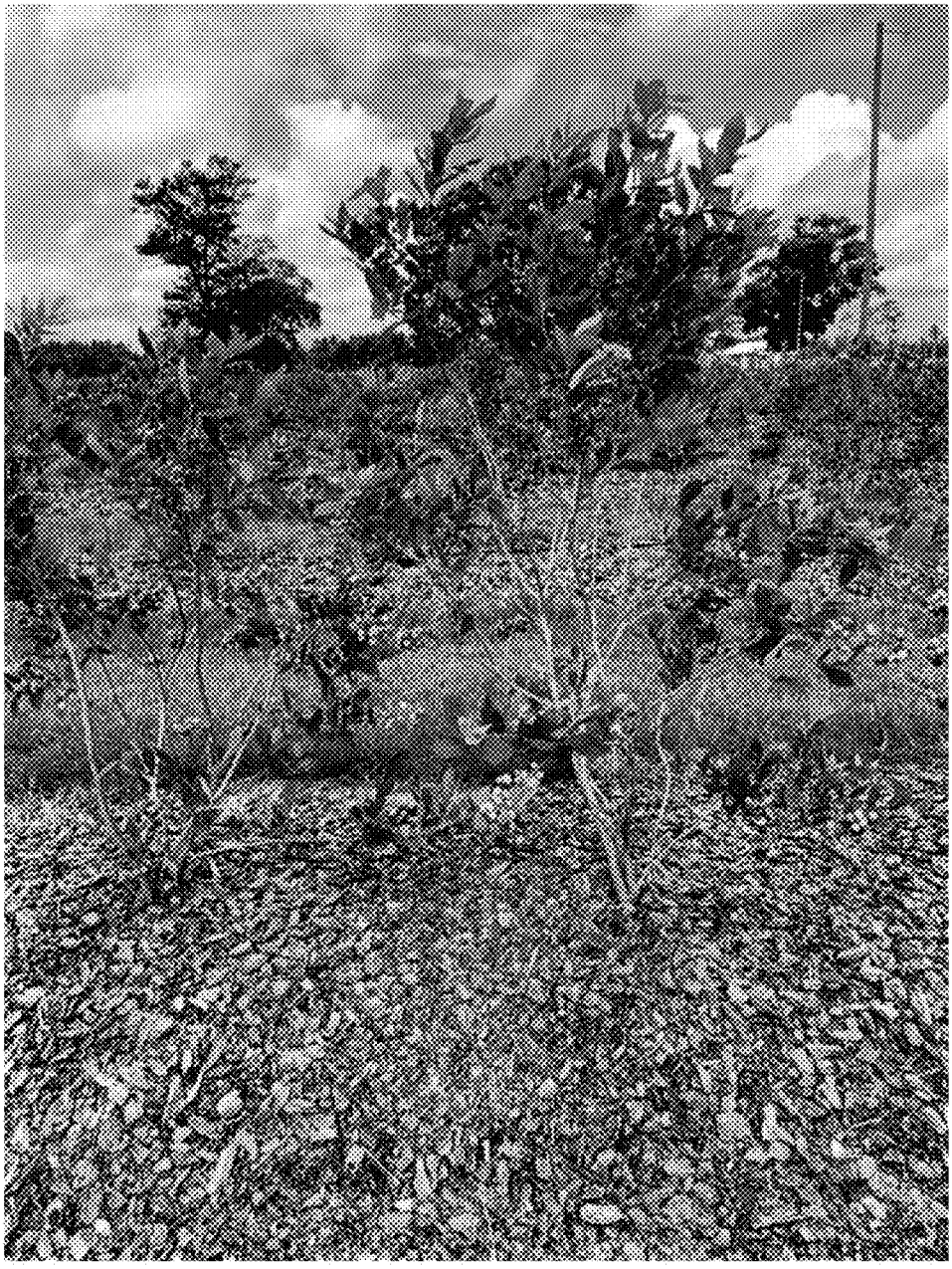

The photograph labeled FIG. 3 depicts 3-year old 'TH-1241' plants during fruit ripening showing large berries. Photographs were taken in May 2021.

Figure 4:
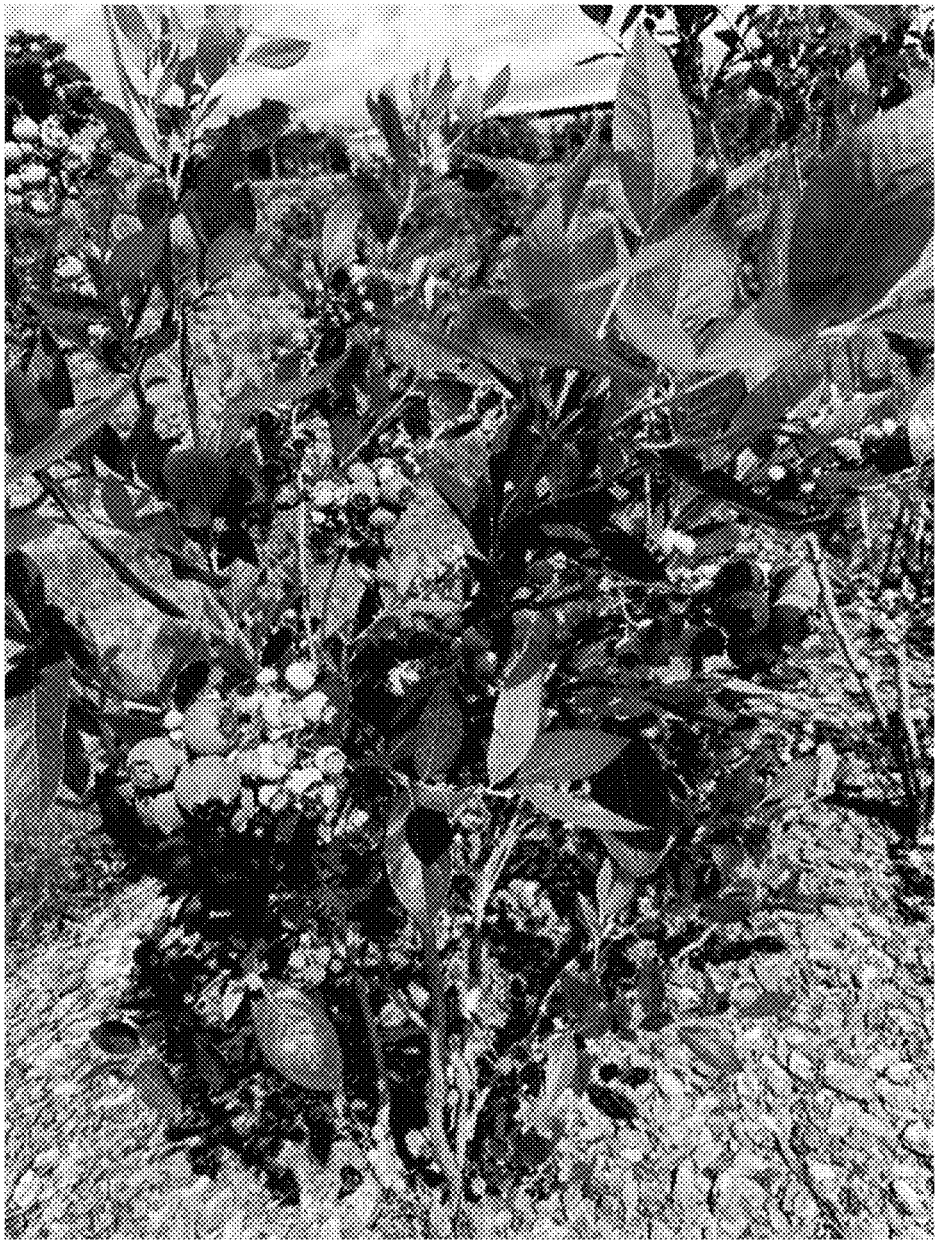

The photograph labeled FIG. 4 depicts a close-up view of 'TH-1241' fruit as it matures showing the large berry size and good color taken in May 2021.

Figure 5A:
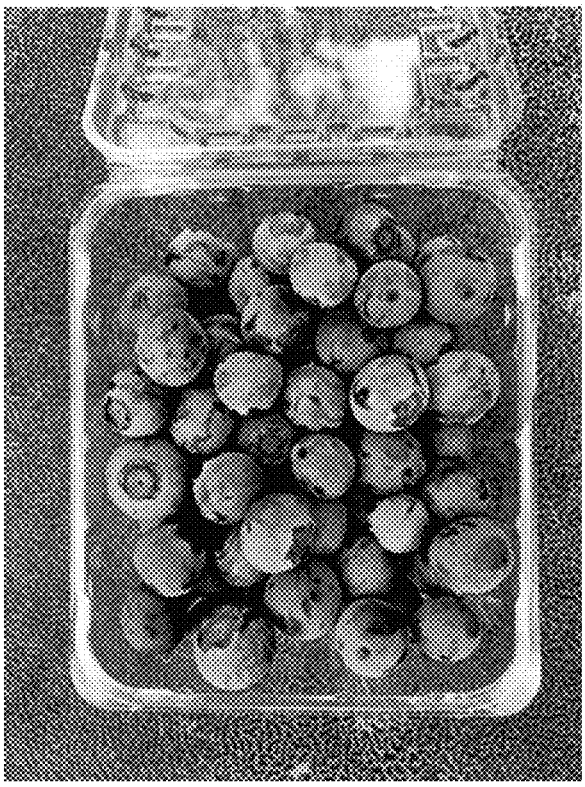
Figure 5B:
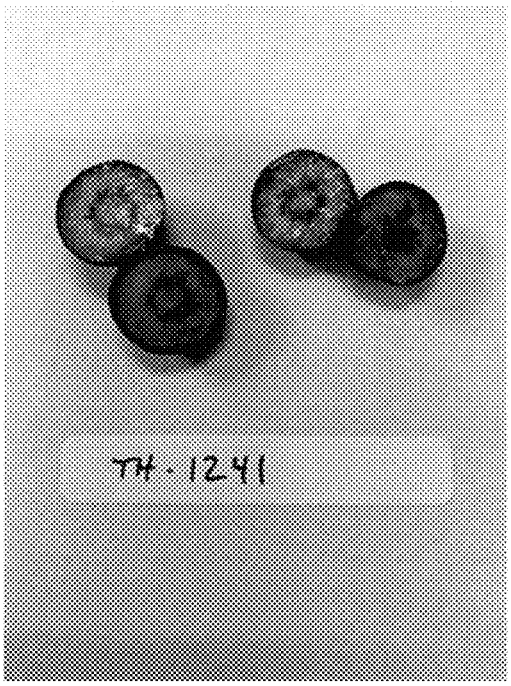

The photographs labeled FIGS. 5A-5B depict close-up views of 'TH-1241' fruit. FIG. 5A is a close-up view of fruit of 'TH-1241' in a container, and FIG. 5B shows a cross sectional view of the interior of the fruit taken in May 2021.

Figure 6:
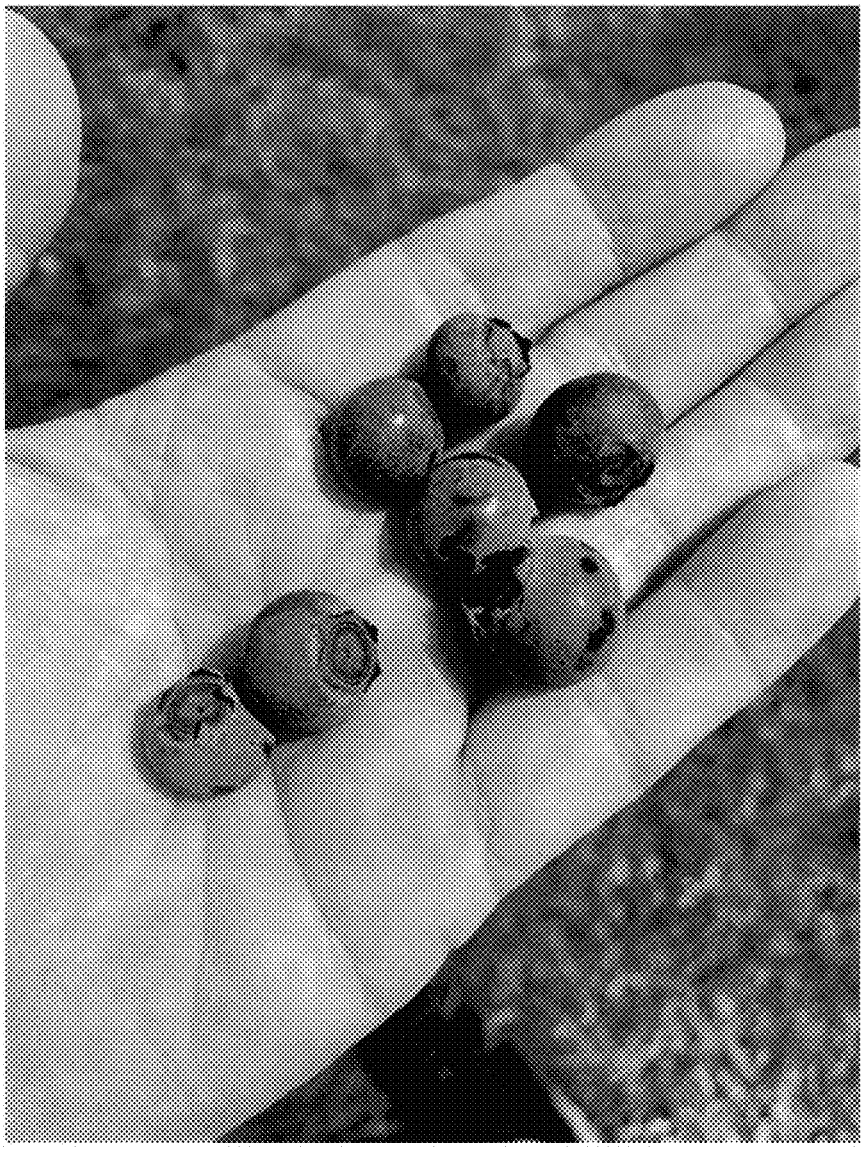

The photograph labeled FIG. 6 depicts a close-up view of ripe fruit of 'TH-1241' in a human hand taken in May 2021.

DETAILED BOTANICAL DESCRIPTION

The following traits have been consistently observed in the original plant of this new variety and in asexually propagated progeny grown in Alapaha and Griffin, Ga., and, to the best knowledge of the inventors, their combination forms the unique characteristics of the new variety *Vaccinium corymbosum* 'TH-1241'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium corymbosum* cultivar named 'TH-1241'. Where dimensions, sizes, colors, and other characteristics are given, it is to be understood that such characteristics are approximations and averages set forth as accurately as practicable. Data were collected between the years of 2017-2021 from horticulture farms and nurseries in Alapaha, Ga. from 3 to 6-year-old plants (planted in the field with supplemental irrigation). In this region, the long-term average annual low temperature ranges from about 54° F. to 58° F., and the average annual high temperature ranges from about 78° F. to 82° F.

Botanical classification: *Vaccinium corymbosum* 'TH-1241'.

*Commercial classification.*—Fruit-bearing shrub.

*Parentage.*—Cross of *Vaccinium corymbosum* 'Star' (U.S. Plant Pat. No. 10,675) and 'Bladen' (non-patented cultivar).

Growth and propagation:

*Propagation type.*—Vegetative by softwood cuttings.

*Growth rate.*—Highly vigorous.

*Root description.*—Fibrous.

Plant description:

*Growth habit.*—Plant is strongly upright, with dominant vertical growth. Open canopy with little tendency to spreading. Two to 4 main canes arising from the original crown with strong vertical growth, followed by multiple branching of shoots from those canes about 20 to 35 cm above ground.

*Usage.*—Commercial fruit production primarily.

*Productivity.*—Medium to high yielding. Yields of about 4 to 8 lbs per plant each year on plants 4 years old or older grown under well fertilized and irrigated field conditions. Frost protection may be useful to reach yield potential in some years.

*Size of plant.*—Plant is about 1.5 to 1.8 m tall by about 4 years. The plant crown, or base, is narrow, typically about 10 to 20 cm in diameter. Upper portion of plant canopy reaches about 1.0 to 1.4 m in diameter by about 4 years.

*Cold hardiness.*—Similar to southern highbush varieties such as Star (U.S. Plant Pat. No. 10,675) and 'Rebel' (U.S. Plant Pat. No. 18,138).

*Disease resistance.*—No exceptional disease resistance or susceptibility observed. Typical for early season southern highbush such as 'Rebel' and 'Star'.

*Chilling requirement.*—Plants are medium chill, requiring an estimated 350 to 450 hours, or more, of temperatures at or below 45° F. (7° C.) to induce normal leafing and flowering during the spring under conventional dormant production systems. The chill requirement is somewhat less than the female parent 'Star' (400 to 500 hours of chilling required) and much less than the male parent 'Bladen' (non-patented variety; 650 to 700 hours of chilling required).

*Leafing.*—Plants tend to break sufficient leaf buds simultaneously with, or shortly after, anthesis.

*Canes.*—Main cane base diameter about 15 to 25 mm, color most near Grey 201C; two-year-old cane diameter about 10 to 15 mm, color transitioning from Yellow Green 145A to Greyed Orange 166B; current season wood diameter about 3 to 8 mm, color Yellow Green 145A; one-year-old shoots have the same color as current season shoots, Yellow Green 145A.

*Fruiting wood.*—Moderate number of twigs (5 to 10 common) of about 15 to 25 cm in length, with internode lengths of about 20 to 25 mm common; plants flower and fruit on one-year-old shoots.

Foliage:

*Leaf color healthy mature leaves.*—Top side of leaf color is Green N137C, under side of leaf color is Green 138B.

*Leaf arrangement.*—Alternate, simple.

*Leaf shape.*—Nearly elliptic.

*Leaf margins.*—Nearly entire.

*Leaf venation.*—Pinnate with slight netting.

*Leaf apices.*—Broadly acuminate.

*Leaf bases.*—Acute.

*Leaf dimensions.*—Length: about 55 to 75 mm; width: about 25 to 35 mm.

*Petioles.*—Small, about 4.0 to 5.0 mm long, about 1.0 to 1.5 mm wide; Color: Yellow Green 145C.

*Texture.*—Leaf margins, nearly entire; both upper and lower leaf surfaces, glaucous.

Flowers:

*Date of* 50% *anthesis.*—3-year average March 7 in southeast Georgia.

*Flower shape.*—Urceolate; average inflorescence length is about 5.0 to 10.0 mm.

*Flower bud.*—Number: high to very high, averaging about 4 to 7 buds per fruiting shoot; anthocyanin coloration is medium to strong.

*Flowers per cluster.*—About 5 to 8 common.

*Flower fragrance.*—Light cinnamon and/or rose fragrance often observed.

*Corolla color.*—White N155D; streaks of Red Purple 63B can often be observed prior to full corolla expansion and flower opening.

*Corolla length.*—About 8.0 to 9.0 mm.

*Corolla width.*—About 7.0 to 8.0 mm.

*Corolla aperture width.*—About 4.5 to 5.0 mm.

*Flower peduncle.*—Length about 5.0 to 10.0 mm; Color: Yellow Green 145C; streaks of Red Purple 63B often observed around the time of flowering.

*Flower pedicel.*—Length about 4.5 to 5.5 mm; Color: Yellow Green 145C to Green 138C; streaks of Greyed Purple 186B often observed around the time of flowering.

*Calyx* (*with sepals*).—Diameter: about 8.0 to 9.0 mm; Color: sepals primarily Green 138C, with occasional streaks of Greyed Purple 186B; calyx center Green 138B.

*Stamen.*—Length: about 6.5 to 7.5 mm; number per flower: about 10; filament color: Green White 157C.

*Style.*—Length: about 9.0 to 10.0 mm; Color: Yellow Green 145B.

*Pistil.*—Length: about 11.0 to 12.0 mm; ovary color: Green 138C.

*Anther.*—Length: about 3.0 to 3.5 mm; number: 10; Color: Greyed Orange 165B.

*Pollen.*—Abundance: high; Color: Yellow White 158A to 158B.

*Compatibility.*—The cultivar has a moderate degree of self-compatibility.

Fruit:

*Date of* 50% *maturity.*—3-year average April 30 in southeast Georgia.

*Fruit development period.*—About 54 days in southeast Georgia.

*Berry color.*—With wax Violet Blue 98D; with wax removed Black 203C.

*Berry flesh color.*—White 155C.

*Berry surface wax abundance.*—High.

*Berry weight.*—$1^{st}$ harvest: about 2.8 to 3.2 g; $2^{nd}$ harvest: about 2.2 to 2.6 g.

*Berry size.*—Height from calyx to scar: about 15 to 17 mm; diameter: about 18 to 21 mm.

*Berry shape.*—Semi-spherical to semi-disk shaped.

*Fruit stem scar.*—Small to medium, dry, with occasional small tear upon harvest.

*Calyx.*—Depth medium, less than about 1.0 mm; width medium, about 8.0 to 11.0 mm; sepals often present, turned mostly inwards and flat, occasional semi-erect, about 1.0 to 1.5 mm.

*Berry firmness.*—Medium to good firmness.

*Berry flavor and texture.*—Aromatic, slightly sweet, mildly acid flavor; occasional "peachy" flavor experiences; smooth texture.

*Storage quality.*—Good (10-12 days).

*Suitability for mechanical harvesting.*—Not likely suitable.

*Uses.*—Primarily intended for fresh fruit for shipping and processing markets.

Seed:

*Seed abundance in fruit.*—Low to medium, with less than about 10 fully developed seeds/berry.

*Seed color.*—Greyed Orange 164A.

*Seed dry weight.*—About 34.4 mg per 100 seed.

*Seed size.*—About 1.0 to 1.5 mm long.

It is claimed:

1. A new and distinct cultivar of the *Vaccinium* plant named 'TH-1241' as illustrated and described herein.

* * * * *